(12) United States Patent
Spitzer (10) Patent No.: US 8,565,889 B2
(45) Date of Patent: Oct. 22, 2013

(54) METHOD FOR FITTING A COCHLEAR IMPLANT WITH PATIENT FEEDBACK

(75) Inventor: Philipp Spitzer, Innsbruck (AT)

(73) Assignee: Med-El Elektromedizinische Gereate GmbH, Innsbruck (AT)

( * ) Notice: Subject to any disclaimer, the term of this patent is extended or adjusted under 35 U.S.C. 154(b) by 984 days.

(21) Appl. No.: 12/632,878

(22) Filed: Dec. 8, 2009

(65) Prior Publication Data

US 2010/0145411 A1 Jun. 10, 2010

Related U.S. Application Data

(60) Provisional application No. 61/120,636, filed on Dec. 8, 2008.

(51) Int. Cl.
*A61N 1/36* (2006.01)

(52) U.S. Cl.
CPC ......... *A61N 1/36032* (2013.01); *A61N 1/36132* (2013.01)
USPC .............................................. 607/57; 607/59

(58) Field of Classification Search
USPC ......................... 607/55–57, 59, 63
See application file for complete search history.

(56) References Cited

U.S. PATENT DOCUMENTS

| | | | |
|---|---|---|---|
| 4,515,158 A | 5/1985 | Patrick et al. | 128/419 R |
| 4,577,641 A | 3/1986 | Hochmair et al. | 128/746 |
| 5,434,924 A | 7/1995 | Jampolsky et al. | 381/68.4 |
| 6,157,861 A | 12/2000 | Faltys et al. | 607/57 |
| 7,149,583 B1 | 12/2006 | Litvak | 607/57 |
| 7,209,789 B2 | 4/2007 | Zierhofer | 607/57 |
| 7,225,027 B2 | 5/2007 | Zeng et al. | 607/57 |
| 7,251,530 B1 | 7/2007 | Overstreet et al. | 607/55 |
| 7,292,892 B2 | 11/2007 | Litvak et al. | 607/57 |
| 7,310,558 B2 | 12/2007 | Hoesel | 607/57 |
| 7,421,298 B2 | 9/2008 | Daly et al. | 607/57 |
| 2001/0014818 A1 | 8/2001 | Kennedy | 607/57 |

(Continued)

FOREIGN PATENT DOCUMENTS

| | | | |
|---|---|---|---|
| EP | 1338301 | 2/2002 | A61N 1/36 |
| WO | WO 9949815 | 10/1999 | A61F 2/18 |
| WO | WO 0119135 | 3/2001 | H04R 25/00 |
| WO | WO 0119304 | 3/2001 | A61F 11/04 |

OTHER PUBLICATIONS

McKay, Colette, et al, "The effect of rate of stimulation on perception of spectral shape by cochlear implantees", *Journal of Acoustical Society of America*, AIP/Acoustical Society of America, Melville, NY, US, vol. 118; No. 1; Jan. 1, 2005, pp. 386-392; XP012073185; ISSN: 001-4966.

(Continued)

*Primary Examiner* — Carl H Layno
*Assistant Examiner* — Jessica Sarcione
(74) *Attorney, Agent, or Firm* — Sunstein Kann Murphy & Timbers LLP (57) ABSTRACT

An audio prostheses having a set of operating parameters is fit to an implanted patient. An audio stimulation pattern is initiated to the audio prosthesis. A fit adjustment process is performed during the audio stimulation pattern, which includes: changing a set of selected operating parameter values. Patient feedback is received that indicates a subjective performance evaluation of operation of the audio prosthesis. The process is repeated (e.g., continuously) to collect performance evaluation data related to the operating parameter values. Then the operating parameters are set based on the performance evaluation data.

16 Claims, 4 Drawing Sheets

(56) References Cited

U.S. PATENT DOCUMENTS

| | | | |
|---|---|---|---|
| 2002/0048374 A1 | 4/2002 | Soli et al. | 381/60 |
| 2005/0088435 A1 | 4/2005 | Geng | 345/419 |
| 2005/0107843 A1 | 5/2005 | McDermott et al. | 607/57 |
| 2005/0203589 A1 | 9/2005 | Zierhofer | 607/57 |
| 2005/0245991 A1 | 11/2005 | Faltys et al. | 607/57 |
| 2006/0052841 A1 | 3/2006 | Daly et al. | 607/57 |
| 2006/0100672 A1 | 5/2006 | Litvak | 607/57 |
| 2006/0265061 A1 | 11/2006 | Kwon et al. | 623/10 |
| 2008/0021551 A1* | 1/2008 | Overstreet et al. | 623/10 |
| 2008/0172108 A1 | 7/2008 | Zierhofer et al. | 607/57 |
| 2008/0249589 A1 | 10/2008 | Cruz et al. | 607/57 |
| 2008/0300653 A1* | 12/2008 | Svirsky | 607/57 |
| 2010/0198300 A1 | 8/2010 | Smith | 607/57 |
| 2010/0198301 A1 | 8/2010 | Smith | 607/57 |

OTHER PUBLICATIONS

Ziese, M., et al, "Speech Understanding with the CIS and the n-of-m Strategy-in the MED-EL COMBI 40+ System", *ORL*, 2000;62:321-329.

Commissioner of Patents, International Search Report and Written Opinion, PCT/US2009/067073, Jan. 26, 2010.

\* cited by examiner

METHOD FOR FITTING A COCHLEAR IMPLANT WITH PATIENT FEEDBACK

This application claims priority from U.S. Provisional Patent Application 61/120,636, filed Dec. 8, 2008, which is incorporated herein by reference.

FIELD OF THE INVENTION

The present invention relates to medical implants, and more specifically to fit customization in audio prosthesis systems such as cochlear implant systems.

BACKGROUND ART

Figure 1:
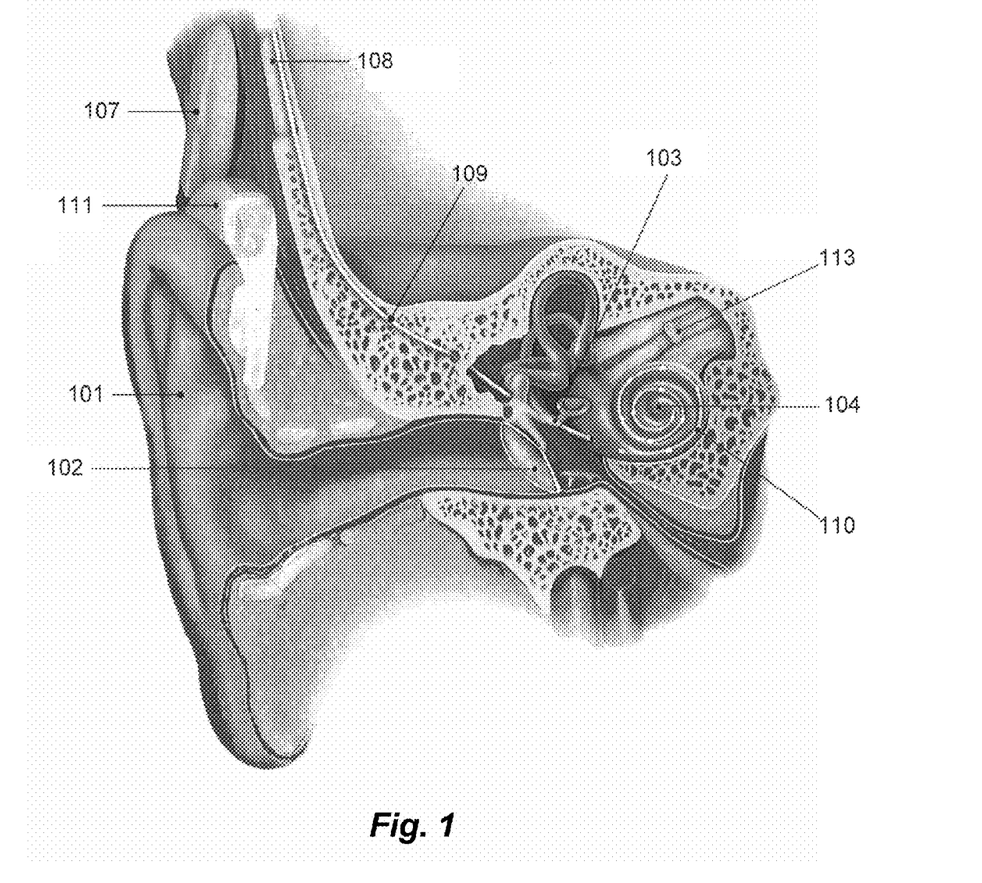
FIG. 1 shows structures in a normal human ear and some components of a typical cochlear implant system.

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrodes on its surface that provide selective stimulation of the cochlea 104.

Cochlear implant systems employ stimulation strategies that provide high-rate pulsatile stimuli in multi-channel electrode arrays. One specific example is the "Continuous Interleaved Sampling (CIS)"-strategy, as described by Wilson et al., *Better Speech Recognition With Cochlear Implants*, Nature, vol. 352:236-238 (1991), which is incorporated herein by reference. For CIS, symmetrical biphasic current pulses are used, which are strictly non-overlapping in time. The rate per channel typically is higher than 800 pulses/sec. Other stimulation strategies may be based on simultaneous activation of electrode currents. These approaches have proven to be successful in giving high levels of speech recognition.

For an audio prosthesis such as a cochlear implant to work correctly, some patient-specific operating parameters need to be determined in a fit adjustment procedure where the type and number of operating parameters are device dependent and stimulation strategy dependent. Possible patient-specific operating parameters for a cochlear implant include:

$THR_1$ (lower detection threshold of stimulation amplitude) for Electrode 1
$MCL_1$ (maximum comfortable loudness) for Electrode 1
Phase Duration for Electrode 1
$THR_2$ for Electrode 2
$MCL_2$ for Electrode 2
Phase Duration for Electrode 2
. . .
Pulse Rate
Number of fine structure channels
Compression
Parameters of frequency→electrode mapping
Parameters describing the electrical field distribution Some fit adjustment procedures allow applying the changes to the operating parameter without notable delay ("live-voice"); e.g. Willeboer and Smoorenburg, *Comparing Cochlear Implant Users' Speech Performance With Processor Fittings Based On Conventionally Determined T And C Levels Or On Compound Action Potential Thresholds And Live-Voice Speech In A Prospective Balanced Crossover Study*; Ear Hear, 27(6):789-798, December 2006; incorporated herein by reference.

Other types of audio prostheses have similar such parameters that need to be fit to the patient. For example, besides cochlear implant systems as such, some subjects with some residual hearing (partial deafness) are now benefiting from combined electric and acoustic stimulation (EAS) such as was first described in von Ilberg et al., *Electric-Acoustic Stimulation Of The Auditory System*, ORL 61:334-340 (1999), which is incorporated herein by reference. EAS systems combine the use of a conventional hearing aid (HA) device to provide acoustic-mechanical stimulation of lower audio frequencies to the subject's ear drum and a cochlear implant (CI) to provide intracochlear electrical stimulation of higher audio frequencies to the auditory nerve. For example, see Lorens et al., *Outcomes Of Treatment Of Partial Deafness With Cochlear Implantation: A DUET Study*, Laryngoscope, 2008 February: 118(2):288-94, which is incorporated herein by reference.

One common method for fit adjustment is to behaviorally find the threshold (THR) and maximum comfortable loudness (MCL) value for each separate stimulation electrode. See for example, Rätz, *Fitting Guide for First Fitting with MAESTRO 2.0*, MED-EL, Fürstenweg 77a, 6020 Innsbruck, 1.0 Edition, 2007. AW 5420 Rev. 1.0 (English_EU); incorporated herein by reference. Other alternatives/extensions are sometimes used with a reduced set of operating parameters; e.g. as suggested by Smoorenburg, *Cochlear Implant Ear Marks*, University Medical Centre Utrecht, 2006; U.S. Patent Application 20060235332; which are incorporated herein by reference. In normal operation, only stimulation amplitudes between MCL and THL for each channel are used. The dynamic range between MCL and THL typically is between 6-12 dB. However, the absolute positions of MCLs and THLs vary considerably between patients, and differences can reach up to 40 dB. To cover these absolute variations, the overall dynamic range for stimulation in currently used implants typically is about 60 dB.

There are several methods of setting fitting parameters like MCLs and THLs. For example, they can be estimated during the fit adjustment procedure by applying stimulation pulses and asking the patient about his/her subjective impression. Other more subjective fit adjustment procedures are also used, such as those which determine the syllable/word/sentence recognition score of users (e.g. "Freiburger Sprachtests", "Göttinger Satztest", "Einsilber-Reimtest nach von Wallenberg and Kollmeier"). The outcome of these tests can be used to monitor the performance of a user over time and to compare different settings of the fitting. In general, these tests are time consuming and a whole test session is required for each "setup" of the fitting.

These methods usually work without problems with postlingually deaf patients. However, problems can occur with prelingually or congenitally deaf patients, and in this group all ages—from small children to adults—are concerned. These patients are usually neither able to interpret nor to describe hearing impressions, and only rough estimations of fitting parameters like MCLs and THLs based on behavioral methods are possible. Especially the situation of congenitally deaf small children needs to be mentioned here. An adequate acoustic input is extremely important for the infant's speech and hearing development, and this input in many cases can be provided with a properly fitted cochlear implant. Moreover, the fitting procedure can be very time consuming and difficult, especially for children. Sometimes objective measurements are used to assist in the fitting procedure. These include:

nerve responses to electrical stimulation
brainstem responses
electrically evoked stapedius reflexes Sometimes these methods are combined. However, these objective measures do not determine the user experience/performance and do not optimize the fitting regarding user experience/performance.

One approach for an objective measurement of MCLs and THLs is based on the measurement of the EAPs (Electrically Evoked Action Potentials), as described by Gantz et al., *Intraoperative Measures of Electrically Evoked Auditory Nerve Compound Action Potentials*, American Journal of Otology 15 (2):137-144 (1994), which is incorporated herein by reference. In this approach, a recording electrode in the scala tympani of the inner ear is used. The overall response of the auditory nerve to an electrical stimulus is measured very close to the position of the nerve excitation. This neural response is caused by the super-position of single neural responses at the outside of the axon membranes. The amplitude of the EAP at the measurement position is between 10 µV and 1800 µV. Information about MCL and THL at a particular electrode position can first of all be expected from the so called "amplitude growth function," as described by Brown et al., *Electrically Evoked Whole Nerve Action Potentials In Ineraid Cochlear Implant Users: Responses To Different Stimulating Electrode Configurations And Comparison To Psychophysical Responses*, Journal of Speech and Hearing Research, vol. 39:453-467 (June 1996), which is incorporated herein by reference. This function is the relation between the amplitude of the stimulation pulse and the peak-to-peak voltage of the EAP.

Another interesting relation is the so called "recovery function" in which stimulation is achieved with two pulses with varying interpulse intervals. The recovery function as the relation of the amplitude of the second EAP and the interpulse interval allows conclusions to be drawn about the refractory properties and particular properties concerning the time resolution of the auditory nerve.

One problem of existing fit adjustment procedures is that they either don't optimize the fitting at all, or at most just for speech perception. And the subjective judgment of the patients is not used as it could or should be.

SUMMARY OF THE INVENTION

Embodiments of the present invention are directed to a method for fitting to a patient user an audio prostheses having a set of operating parameters. An audio stimulation pattern is initiated to the audio prosthesis. A fit adjustment process is performed during the audio stimulation pattern, which includes: changing a set of selected operating parameter values. Patient feedback is received that indicates a subjective performance evaluation of operation of the audio prosthesis. The process is repeated (e.g., continuously) to collect performance evaluation data related to the operating parameter values. Then the operating parameters are set based on the performance evaluation data.

The operating parameter values may be changed continuously and the patient feedback may be received continuously. Or the operating parameter values may be changed in discrete steps after receiving the patient feedback. The operating parameter values are changed sequentially or simultaneously. The operating parameter values may be changed by the patient or by fit adjustment software, e.g., based on a Levenberg Marquardt Algorithm.

The patient feedback may be received continuously. The subjective performance evaluation may be based on a comparison to operation of the audio prosthesis according to a set of reference operating parameter values. In addition or alternatively, the patient feedback can be based on one or more of a subjective instantaneous judgment without comparison, comparison to a previous set of parameters, and/or comparison to user selected parameters. The audio prosthesis may be a cochlear implant, a digitally programmed conventional hearing aid, or a hybrid acoustic-electrical stimulation system. The audio stimulation pattern may be in a native language or in a foreign language and may be from one or more of live music and/or speech, music and/or speech from a CD, cocktail party background, noise, television, radio, the patient's own voice (e.g. reading a book), and/or the patient's playing of a music instrument.

DETAILED DESCRIPTION OF SPECIFIC EMBODIMENTS

Various embodiments of the present invention are directed to improved techniques for a dynamic fit adjustment of an audio prosthesis for a given patient user. In the following discussion the system operating parameters will be referred to as $p_1, p_2, \ldots, p_N$. Each of the operating parameters can be discrete or continuous with optional bottom and top boundaries. Let $s_i(p_1, \ldots, p_N)$ be a subjective operating parameter judgment value that measures the "music enjoyment." There are many such possible subjective judgment values such as: $s_2$="pop music enjoyment", $s_3$="speech understanding in quiet", $s_4$="quality and clearness of speech", etc. The objective of the fitting process is to maximize $s_1$ (or any other $s_X$ function). If $s_1$ were a known mathematical formula, then this problem would be a (probably nonlinear) fitting problem for which mathematical methods exist. See, e.g., Levenberg Marquardt Algorithm as described in Marquardt, D. W., *An algorithm for Least-Square Estimation of Nonlinear Parameters*, Journal of the Society for Industrial and Applied Mathematics, Society for Industrial and Applied Mathematics, 2, 431-441, 1963; incorporated herein by reference. For nonlinear fits, the determination of the starting conditions is important to quickly and successfully finding a solution, and when choosing non-optimal initial operating parameters, the algorithm may end up in a local maximum of $s_1$ that is not the global maximum.

An existing fit procedure as used in the prior art would be:
Use a set of parameters $P_1 = (p_1, \ldots, p_N)$ and do a speech understanding test.
Alter one parameter $p_i \Rightarrow P_2$ and do another speech understanding test.
If the evaluation is better, then use the new set as the baseline, otherwise, keep the old set.
Repeat the procedure for different parameters.

Embodiments of the present invention let the patient user dynamically determine $s_i$ "live."

Figure 2:
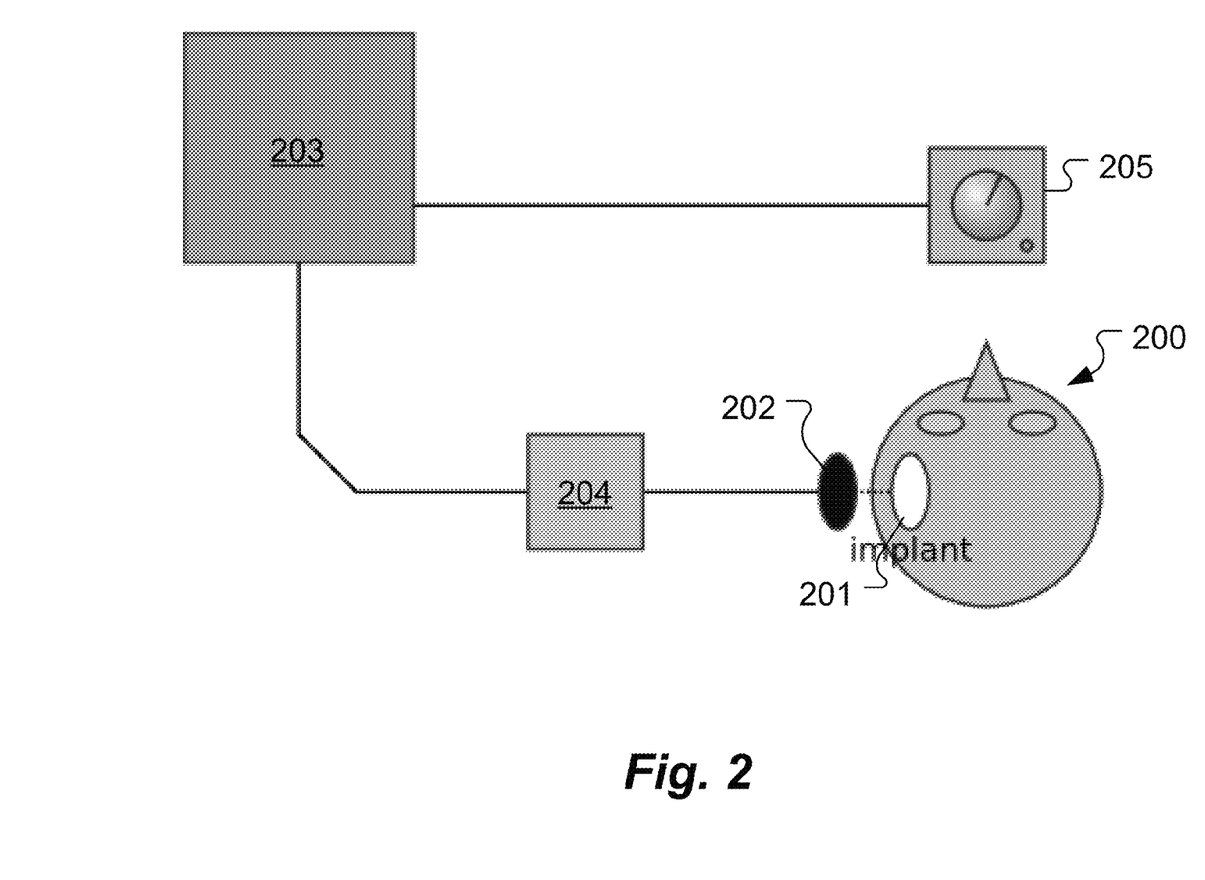
FIG. 2 shows a basic generic embodiment of the present invention.
Figure 4:
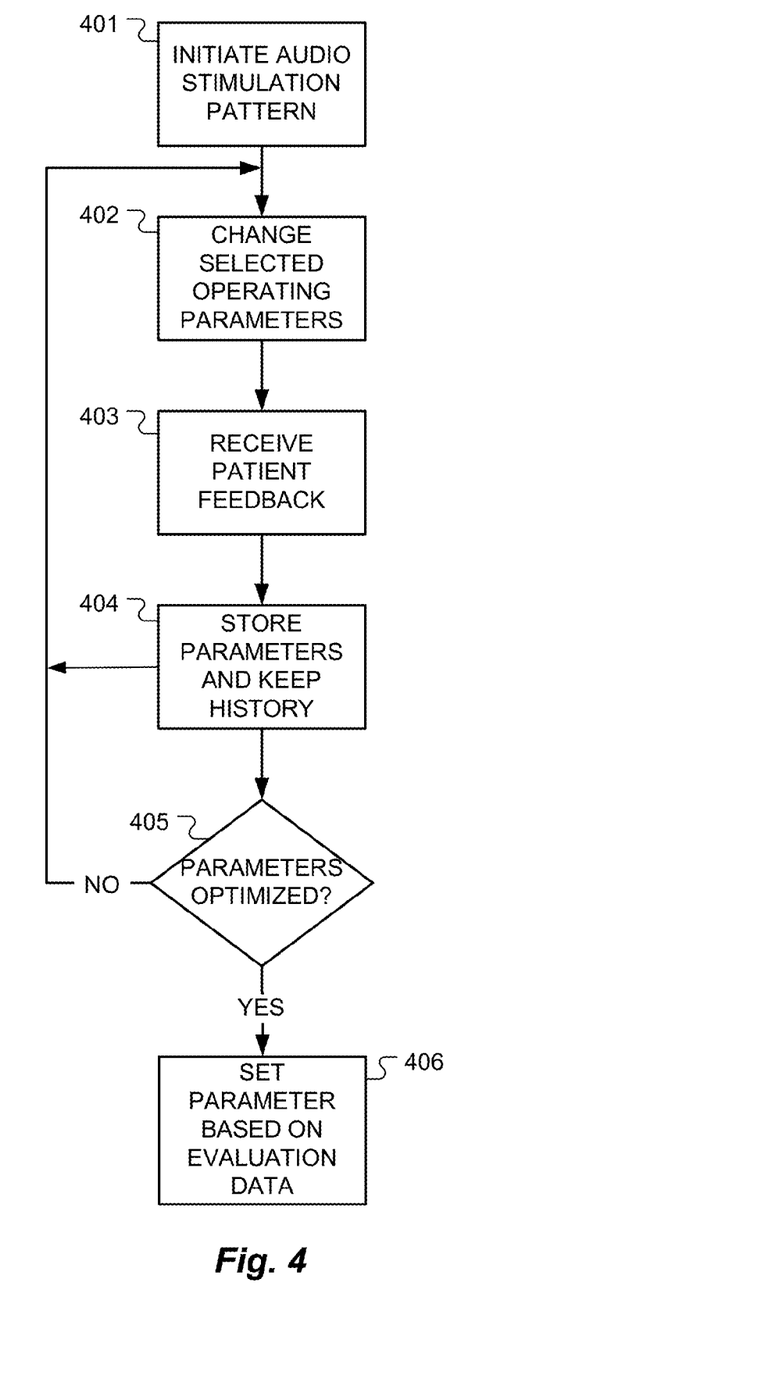
FIG. 4 shows various logical steps in a dynamic feedback fit process according to an embodiment of the present invention.

FIG. 2 shows a basic generic setup and FIG. 4 shows various logical steps in one such a dynamic feedback fit adjustment process according to one embodiment of the present invention. A fit processor 203 initiates an audio stimulation pattern (music, speech, . . . ) for the patient 200, step 401. Specifically, the audio stimulation pattern is delivered from the fit processor 203 via a user interface 204 to the external transmission coil 202 the cochlear implant system. The implant coil 201 receives the stimulation pattern and processes it into one or more stimulus signals for the cochlear implant which are perceived by the patient user 200. The audio stimulation pattern may depend on the specific operating parameters being adjusted and/or the choice of the patient user 200, for example: a prerecorded voice that is continuously reading a book, two people talking with each other continuously in a cocktail party noise setting, continuous music (perhaps of specific types such as classical, pop, rock, etc.), and/or a reference sentence of a voice that can be played on demand.

While delivering the audio stimulation pattern, the values of a set of selected operating parameters are changed, step 402. For example, the fit processor 203 may change the values of the set of selected operating parameters either each one sequentially or all simultaneously, in discrete steps or continuously over time (within certain constraints, e.g. the current of one channel may not exceed a certain level). The fit processor 203 may change the values of the selected operating parameters according to a well known mathematical fitting method, e.g. based on a Levenberg Marquardt Algorithm. Alternatively or in addition, the values of the selected operating parameters may be changed by the patent user 200, for example, where the user can select different sound sources to determine the value of $s_1$ and controls the progression to the next parameter set. In that case, it is helpful to require that the user makes his decision relatively quickly so that many parameter value combinations can be tested. For the determination of subsequent operating parameters $P_2, P_3, \ldots$, the already determined judgment (e.g., $P_1$) of previously determined parameters can be used. The recorded parameters from one or more previous fitting sessions may be stored and used as additional information for the fitting processor 203. In some embodiments, the fitting processor 203 may use an associated database of fittings and parameter judgments from other patients so that the fitting processor has information about typical ranges of parameters and can determine the importance of specific parameters. This can be included, for example, to determine the "next" suggested parameter values in step 402. The allowed ranges for the parameters ($P_1, \ldots, P_N$) as well as additional constraints (values derived from several parameters may also have limits, e.g. the charge per time may not exceed a certain value) may be adjustable. There could be global constraints that can be further limited by the audiologist and/or the patient. Embodiments of the invention should include the possibility to determine these ranges using the well-known methods like e.g. playing a stimulus at adjustable loudness to determine MCL. Embodiments should make it possible to use traditional methods to determine ($P_1, \ldots, P_N$). This could e.g. be used to determine the starting parameters.

The patient user 200 provides patient feedback, step 403, indicating a subjective performance evaluation of operation of the audio prosthesis, e.g. by turning a feedback input 205. The feedback input 205 may take various specific forms such as a hardware implementation—a slider knob (the higher the better), a rotatable knob with or without a scale and/or zero point—the more clockwise, the better, or an input pad where the patient user 200 puts pressure (the more the better), or a software implementation—a virtual input control shown on a computer display and controlled by a mouse or keyboard.

The fit processor 203 records both the values of the operating parameters over time and the corresponding patient feedback performance evaluation data, i.e., the $s_1$ level judged by the user, step 404. In addition the fit processor 203 may re-play previously determined operating parameters to eliminate drift of the $s_1$ signal over time. Alternatively or in addition, the patient user 200 could be asked to judge a reference parameter set every X seconds and/or do comparisons. This process continues until stopped by the user, step 405, when the operating parameter values are set based on the performance evaluation data, step 406. For example, the process may be stopped when:

The patient wants to stop
Audiologist wants to stop
Specific time is over
System has reached values where it cannot find further improvement.

As long as the history is kept by the system a longer "pause" is also possible, even over multiple fitting-sessions.

The fit procedure usefully may be repeated regularly (e.g. every month) to reflect improved experience of the patient user 200 who may have learned to take advantage of a new parameter set and a further optimization may be possible. For example, it may be possible for the patient user 200 to change the operating parameters from home (perhaps with different fit adjustment constraints). In this case, no audiologist has to be involved (i.e., "self-fitting").

Whereas existing fitting strategies maximize speech understanding, embodiments of the present invention better fit the system to account for subjective comfort of the patient and/or sound quality evaluation. Moreover, the patient has something to do and plays an active role in the fitting process, which takes advantage of the patient's strong interest in maximizing the outcome.

The initial settings of the operating parameters are very important in the above, so it may be useful to base the initial parameter values on experience with other patients. Properties of the dynamically fit operating parameter set that can be explored include, without limitation, differences in the $s_1$ signal between parameter changes, absolute value of $s_1$, perhaps corrected by a global drift over time, as partial derivatives according to the operating parameters are needed they can be recorded by altering the parameter alone where the derivative is needed, variance and reproducibility of $s_1$ when the same parameter set is played at different times, and/or types and properties of the audio stimulation pattern.

Figure 3:
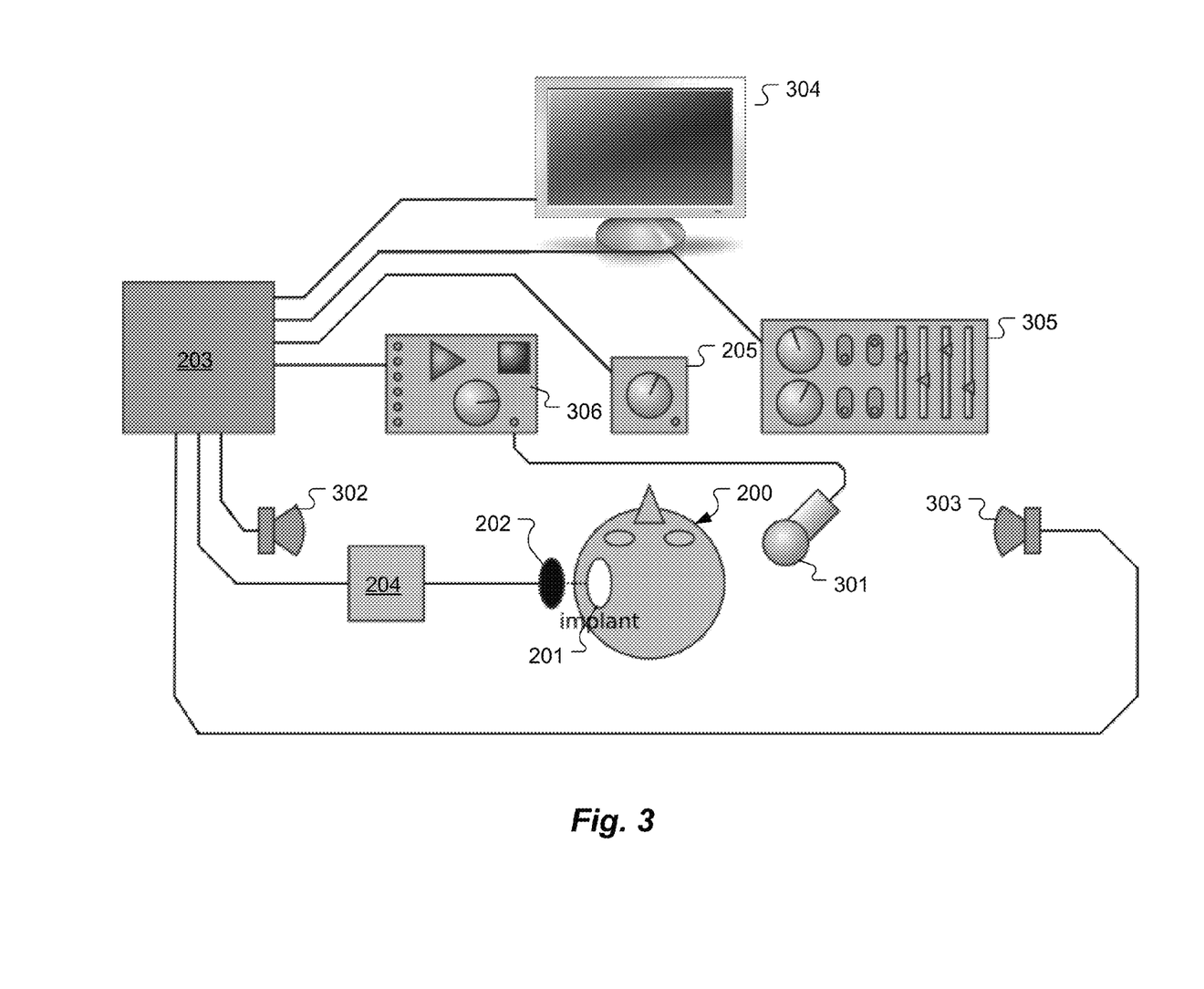
FIG. 3 shows a more advanced embodiment of the present invention.

In addition to the various components present in the basic system shown in FIG. 2, FIG. 3 shows an example of a more detailed fit system which also includes a left speaker 302 and right speaker 303 as a convenience for the testing audiologist to follow the fit process. In addition, patient microphone 301 senses the patient's own voice so that that can be tested and fit. A display screen 304 provides a user interface which allows an audiologist and/or the patient user 200 to control the fit process, e.g., using a mouse and cursor screen arrangement. A fitting parameter module 305 provides various controls and displays for adjustment of the different operating parameters, and an audio source module 306 allows various different audio stimulation patterns from various sources to be controlled and selected.

In further specific embodiments, such methods can be useful for fitting in other circumstances than a generic unilateral cochlear implant. For example, the method can be extended in a bilateral implantation situation to balance two fittings, one on each side. In addition, such a fit process can be useful to provide a combined fitting in a hybrid EAS system. Embodiments can also be used to fit other types of related devices such as a digitally programmed convention hearing aid or a middle ear implant.

Embodiments of the invention may be implemented in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of fitting to a patient an audio prosthesis having a set of operating parameters, the method comprising:
   initiating an audio stimulation pattern to the audio prosthesis;
   performing a fit adjustment process during the audio stimulation pattern, the process including:
   i. continuously changing a set of selected operating parameter values of the audio prosthesis, wherein the operating parameter values are changed sequentially and/or simultaneously
   ii. continuously receiving patient feedback indicating a subjective performance evaluation of operation of the audio prosthesis, and
   iii. repeating the process to collect performance evaluation data related to the operating parameter values; and
   setting the operating parameter values based on the performance evaluation data.

2. A method according to claim 1, wherein the operating parameter values are changed by the patient.

3. A method according to claim 1, wherein the operating parameter values are changed by fit adjustment software.

4. A method according to claim 3, wherein the operating parameter values are changed based on a Levenberg Marquardt Algorithm.

5. A method according to claim 1, wherein the subjective performance evaluation is based on a comparison to operation of the audio prosthesis according to a set of reference operating parameter values.

6. A method according to claim 1, wherein the audio prosthesis is a cochlear implant.

7. A method according to claim 1, wherein the audio prosthesis is a digitally programmed hearing aid.

8. A method according to claim 1, wherein the audio prosthesis is a hybrid acoustic-electrical stimulation system.

9. A system for fitting to a patient an audio prosthesis having a set of operating parameters, the system comprising:
   means for initiating an audio stimulation pattern to the audio prosthesis;
   means for performing a fit adjustment process during the audio stimulation pattern, the process including:
   i. continuously changing a set of selected operating parameter values of the audio prosthesis, wherein the operating parameter values are changed sequentially and/or simultaneously
   ii. continuously receiving patient feedback indicating a subjective performance evaluation of operation of the audio prosthesis, and
   iii. repeating the process to collect performance evaluation data related to the operating parameter values; and
   means for setting the operating parameter values based on the performance evaluation data.

10. A system according to claim 9, wherein the operating parameter values are changed by the patient.

11. A system according to claim 9, wherein the operating parameter values are changed by fit adjustment software.

12. A system according to claim 11, wherein the operating parameter values are changed based on a Levenberg Marquardt Algorithm.

13. A system according to claim 9, wherein the subjective performance evaluation is based on a comparison to operation of the audio prosthesis according to a set of reference operating parameter values.

14. A system according to claim 9, wherein the audio prosthesis is a cochlear implant.

15. A system according to claim 9, wherein the audio prosthesis is a digitally programmed hearing aid.

16. A system according to claim 9, wherein the audio prosthesis is a hybrid acoustic-electrical stimulation system.

* * * * *